United States Patent [19]
Danylewych-May et al.

[11] Patent Number: 5,741,984
[45] Date of Patent: Apr. 21, 1998

[54] METHOD AND APPARATUS FOR SAMPLE COLLECTION BY A TOKEN

[75] Inventors: Ludmila Danylewych-May, North York; Frank J. Kuja, Brampton; John Henry Davies, Port Credit, all of Canada

[73] Assignee: Barringer Technologies Inc., New Providence, N.J.

[21] Appl. No.: 734,234

[22] Filed: Oct. 21, 1996

[51] Int. Cl.$^6$ ........................................................ G01N 1/04
[52] U.S. Cl. ............................................. 73/864.71; 73/864
[58] Field of Search ................... 73/864.71, 864, 73/863.12, 864.81, 23.41; 436/901

[56] References Cited

U.S. PATENT DOCUMENTS

| | | |
|---|---|---|
| 3,970,428 | 7/1976 | Barringer . |
| 4,192,176 | 3/1980 | Barringer . |
| 4,220,414 | 9/1980 | Barringer . |
| 4,909,090 | 3/1990 | McGown et al. . |
| 5,071,771 | 12/1991 | Barbour et al. . |
| 5,405,781 | 4/1995 | Davies et al. . |
| 5,425,263 | 6/1995 | Davies et al. . |
| 5,476,794 | 12/1995 | O'Brien et al. . |
| 5,571,976 | 11/1996 | Drolet .................................. 73/864.71 |

OTHER PUBLICATIONS

B.C. Dionne et al., "Vapor Pressure of Explosives", in Journal of Energetic Materials, vol., 4, pp. 447–472 (1986). Edward E. A. Bromberg et al., "Vapor Sampling Using Controlled Heating", in Proceedings of the First International Symposium on Explosive Detection Technology, Nov. 13–15, pp. 552–558 (1991).

J.M.F. Douse, "Improved Method for the Trace Analysis of Explosives by Silica Capillary Column Gas Chromatography with Thermal Energy Analysis Detection", in Journal of Chromatography, pp. 181–189 (1987).

D.P. Rounbehler et al., "Trace Determination of Amines and Other Nitrogen Containing Compounds with a Modified Thermal Energy Analyzer (TEA™)", in Chromatographia, vol. 16, pp. 354–358 (1982).

*Primary Examiner*—Hezron E. Williams
*Assistant Examiner*—Nashmiya Ashraf
*Attorney, Agent, or Firm*—Bereskin & Parr

[57] ABSTRACT

An apparatus for the collection of a chemical sample from the fingers of an individual for subsequent analytical analysis comprises a token having a base and a substrate on the base. The substrate defines an area such that when the token is removed from a token dispenser the fingers of the individual come into contact with the substrate. Sufficient force must be applied by the fingers of the individual to the substrate when the token is removed from the token dispenser that a chemical sample is transferred from the fingers of the individual to the substrate. The token is then presented for analysis. The substrate may be polytetrafluoroethylene or cotton. A token handler for use in association with the token and an analyzer is also disclosed. Additionally, a method of using the token to obtain a chemical sample from the fingers of an individual is disclosed.

22 Claims, 3 Drawing Sheets

METHOD AND APPARATUS FOR SAMPLE COLLECTION BY A TOKEN

FIELD OF THE INVENTION

The present invention relates generally to a method and apparatus for sample collection for subsequent analytical analysis, and more particularly, to a method and apparatus for sample collection of trace particles and chemicals from the fingers and hands of an individual for subsequent analytical analysis.

BACKGROUND OF THE INVENTION

There exist various analytical devices for chemical detection of various compounds, such ion mobility spectrometers (IMS), gas chromatographs (GC), liquid chromatographs (LC), mass spectrometers (MS), as well as other devices and methods. These detection devices may be used to detect compounds present on the hands and fingers of individuals, either as traces within particles or as discrete particles or aerosols, droplets within finger oils, or the like.

Unfortunately, the need for trace detection of chemical elements has become necessary with the advent of terrorism, where explosives can be concealed to create bombs which are difficult to detect, and also with drug smugglers concealing their drug shipments. Modern, high power explosives are often made with plastic materials, which have extremely low vapour pressures, which make such compounds very difficult to detect through vapour detection. Plastic explosives have vapour pressures approximately five orders of magnitude lower than traditional volatile explosives such as nitroglycerine and trinitrotoluene. In addition, illicit drugs often also have very low vapour pressures and are equally undetectable by vapour detection instruments. Vapour detection devices have been proposed, for example see U.S. Pat. No. 4,909,090 which teaches the use of a hand operated vapour sampler which heats the surface from which the sample is to be collected to assist in dislodging vapours which are trapped on collector surfaces in the vapour sampler. However, this method and apparatus disclosed in this reference does not work with plastic explosives or drugs.

Extremely low levels of explosives or narcotics down to picograms can be detected by various analytical techniques if they can be collected and presented in a manner similar to particle collection analysis. There have been various particle collection techniques which have been previously proposed, such as in assignee's earlier U.S. Pat. Nos. 3,970,428; 5,425,263; 4,220,414; and 4,192,176, the contents of all of which are hereby incorporated by reference.

For example, U.S. Pat. No. 5,476,794 describes particle sample collection with a glove. Other collection techniques have been proposed, including collection with a dust pan-brush arrangement, vacuum suction onto substrates, filters and membranes, swabs, swipes, and finger mitts.

However, each of these apparatus and methods have a disadvantage, in that they require an intermediate step to transfer from the collection substrate the particles and trace chemicals to the analytical device. This requires direct contact of the operator's hands with the substrate media unless protective gloves are used. For example, U.S. Pat. No. 5,476,794 shows using a suction device to vacuum the glove or mitt on which the sample collection is retained. However, this intermediate stage is inefficient, causing a loss of sample due to incomplete transfer from the glove. Further, the use of vacuum suction is inconvenient, in that it is noisy, and requires power for suction. Additionally, suction devices may become contaminated and must be cleaned thoroughly after any positive identification. As well, the suction causes fibres to be released from the substrate, which can obstruct the collecting substrate, and present interfering chemicals or lint which might compete in the analytical process. When IMS is used, matrix residues from the hand covering material often aggressively compete in the desorption efficiency and ionization process, thereby reducing detection efficiencies.

Sample materials or cloth covers for fingers are also used for collecting particles, but leave the fingers vulnerable to sharp or hard objects. In addition, the operator's hand may contaminate the sampling substrate through direct contact. In addition, finger swabs and hand mitts can become dislodged during the sample collection process. Finally, they have limitation in that they may not be effectively used with individual travellers, i.e. they cannot sensibly be used to obtain a sample directly from a person's skin.

Alternatively, samples may be collected directly by suction onto a filter. Generally, the filter is inserted directly into a vacuum suction line to remove particles for analysis. The collection discs are placed immediately behind the suction sampling head to prevent particles entering the suction line and later becoming dislodged so as to give false readings. The collection substrate, however, must be porous enough to allow air suction while remaining dense enough to entrap the particles for detection. During the detection phase, the filter disc may be inserted into a thermal desorption device which is rapidly heated to volatize the collected material, which is then chemically analyzed by IMS, MS, GC, or the like. This technique is disadvantageous in that it requires the presence of relatively loose particles of analytes of interest or dust particles contaminated with analytes on the person or item from which the sample is taken. The vacuum method is also impractical for directly sampling passengers and travellers, as might be required at an aviation security screening point.

Air curtains have been employed to collect samples from persons by impinging on the passenger and sweeping away any entrained vapours or particles into a collection trap for subsequent analysis. Sampling rates in this type of device vary from 10 liters per second to 1,000 liters per second and sample sizes vary from 100 liters to 1,000 liters. Since volumes used in detectors are very small, usually less than 1 ml internal volume, the sample volume must be reduced by a very large factor, causing significant losses in sensitivity. In addition, inefficiency of vapour sampling as described above makes this method ineffective.

Low volume air sampling has also been proposed. However, such a sampling method requires the air samples to be obtained very intimately from the passenger being screened, which is often intrusive and not acceptable to ordinary travellers. Such low flow systems pose problems of irreversible adsorption of low volatility explosives on the inner walls of sampling lines which have very small pores to keep response times as fast as possible. To reduce the volume of dilute air samples, trapping the explosive vapours for desorption into gas carrier streams has been attempted. However, selective trapping is an essential feature for any such system. Other methods have used samplers with integral infrared heat sources and infrared pyrometer control. While such methods can be used on certain surfaces able to withstand temperatures of up to 100° C. or greater, it is completely impossible to use on individuals.

The use of walk through sampling techniques is meant to detect the presence of explosives on a person's body in the expectation that some particles could be dislodged or vapours collected. Each of the methods described above is intended only to find explosives carried by the passengers, not trace amounts actually on a person's skin, due to previous handling of explosives.

For security reasons, currently all passengers boarding an aircraft and all carry on luggage are screened for concealed weapons and explosives. This is usually carried out using two different technologies. Passengers are required to pass through a walk through metal detector, which may be followed by a manual inspection using a hand held metal detection or magnetometric wand. In addition, the passengers' luggage and other personal items are passed through an X-ray machine for visual inspection by security personnel. However, modern plastics and plastic explosives used in the construction of explosive devices are increasingly difficult to detect with the above described technologies, even with the most advanced technology being used.

Therefore, the need has arisen for a method and apparatus to collect trace amounts of particles from the hands of individuals, for analysis to determine whether such individuals have previously handled certain chemicals. Ideally, the technique for collecting such a sample should be unobtrusive and readily incorporated into standard checks at airports and the like.

SUMMARY OF THE INVENTION

It is well established that explosives residues on skin, especially when dissolved into the skin, are hard to remove. It is also a well known fact that a person handling explosives is easily and inadvertently contaminated. There are many factors governing the time lapse from initial contamination to the time when explosives are no longer detected. Some of these are: the type of explosives used, the handling time and the person's skin hygiene. Therefore, screening of passenger's hands/fingers could provide important information on possible explosives concealed on that person or in his/her belongings, or of their involvement in handling explosives. Similar trace contamination can result from the handling of narcotics, various substances of abuse and other contraband materials. The present invention is based on the realization that sampling of discs or tokens or the like to determine the exposure of a person to a sought analyte, such as explosives or drugs, affords a quick non-invasive means of screening.

In accordance with the present invention, a token is manually removed from the dispenser by an individual, and subsequently presented for analytical analysis. The finger pressure exerted on the disc or token as it is removed from the dispenser transfers from the fingers of the individual to the token trace skin and analyte particles, which are dissolved in the body oils in the fingers of the individual, thereby providing a sample of at least one of either solid particles, aerosols, droplets and trace chemicals or combinations thereof. In order that the transfer of the trace elements from the fingers of the individual to the token be efficient, a sufficiently high friction force between the fingers and substrate is needed, which dictates the abrasiveness and physical strength of the substrate. The substrate on the disc or token may be any suitable material common as preferably either polytetrafluoroethylene or cotton.

Thus, in accordance with one aspect of the present invention, there is provided a method of collecting a sample from the hand of an individual for analysis, the method comprising:

(a) dispensing a token, which includes a substrate defining an area for contact with the fingers of the individual;

(b) having the individual manually grasp and remove said token, thereby transferring a sample from the fingers of the individual to said substrate;

(c) having the individual release the token; and (d) delivering the token to an analyzer and analyzing the sample on the token, to determine whether said sample includes a predetermined analyte.

Preferably, the token is dispensed by a mechanism which requires a substantial force to be applied to the token to remove it, whereby the individual must firmly grasp the token, thereby causing adequate transfer of a sample to the token.

Advantageously, the token is dispensed from a dispenser containing a plurality of tokens, and after each token is dispensed, a further token is presented for removal by another individual. For this purpose, the tokens are conveniently provided as a continuous strip, and the step (a) of dispensing a token comprises dispensing a token from an end of the strip.

Alternatively, the plurality of tokens are provided in at least one stack, and the step of dispensing the token comprises dispensing a token from the bottom or top of the stack of tokens.

Optionally, the method can include at least one of the additional steps of:

(1) cleaning and pretreating the tokens by one of baking, washing and solvent treatment to remove possible interferents or other impurities; and (2) pretreating the material of the tokens by impregnation which at least one of a solvent and surface active chemicals to enhance the transfer of analytes of interest from an individual's hand to the token, or to trap and selectively to adsorb analytes of interest.

The method can be carried out using a strip of tokens comprising a plurality of tokens joined together along lines of weakness or lines of perforations, the perforations being dimensioned to provide resistance which must be overcome with a force sufficient to remove the token from the dispenser, thereby causing an individual to firmly grasp a token.

The results of step (d) and the detection of one or more predetermined chemical compounds is preferably used to provide at least one of (i) control of the opening and closing of access devices, such as a turnstile, a man trap, a security screening booth or a door and (ii) warning messages, or other output signals.

The present invention can also be applied to tracking who has been in contact with certain objects, indicating removal or tampering of the objects. For this purpose, a tracer material, which is not readily detectable, is deposited on objects to be monitored, which tracer material is readily transported by a person's hands to the token, whereby the method can detect if the individual has been in contact with the objects being monitored.

To facilitate desorption, the method can be carried out using a token formed from one of a metal cloth and material having a conductive coating thereon, to facilitate electrical heating to achieve rapid thermal desorption.

Each token is advantageously identified by an identification marking, optionally comprising one of a number and a bar code so as to associate the individual to the measurement from an individual token, and optionally to at least one of a boarding pass, an entry procedure and passage in a controlled manner through a screening process.

The token can be subject to one of a multiplicity of desorption temperatures and a temperature ramp to selectively release analytes of interest at different temperatures to facilitate the analysis process.

In accordance with another aspect of the present invention, there is provided a plurality of tokens for collecting samples from the hands of individuals for chemical analysis, the tokens comprising an elongate strip of a substrate material, which has substantially uniform thickness and in which the tokens are separated by one another by lines of weakness, wherein the tokens are formed from a material capable of adsorbing substances of interest and desorbing said desired substances in a desired manner without contaminating a sample desorbed from a token, and wherein the lines of weakness are such that, in use, for an individual to remove an end token from a free end of the strip of tokens requires substantial force, thereby requiring the individual to grasp firmly the end token at the free end of the strip so as to leave an adequate sample on the end token.

In accordance with a further aspect of the present invention, there is provided a token for collecting a sample for an individual for analysis and being intended for dispensation from a dispenser, the token comprising: a substrate and at least one reinforcing ring around a periphery of the substrate and bonded to the substrate, to reinforce and to strengthen the token.

Preferably, the substrate is generally circular and the token includes two annular reinforcing rings on either sides thereof.

Yet another aspect of the present invention provides an apparatus for obtaining and analyzing a sample from an individual, the apparatus comprising: an analyzer having an inlet for receiving a token bearing a sample; a transfer table means including a plurality of different locations including, at least: a first position for an individual to deposit a token, a second position adjacent the inlet of the analyzer for desorption and analysis, and a third position for cooling and removal of a token after analysis, and optionally a fourth position for cleaning and treatment of a token prior to reuse thereof.

BRIEF DESCRIPTION OF THE DRAWINGS

For a better understanding of the present invention and to show more clearly it may be carried into effect, reference will now be made, by way of example, to the accompanying drawings, which show preferred embodiments of the present invention and in which.

DETAILED DESCRIPTION OF THE PREFERRED EMBODIMENT

Figure 1A:
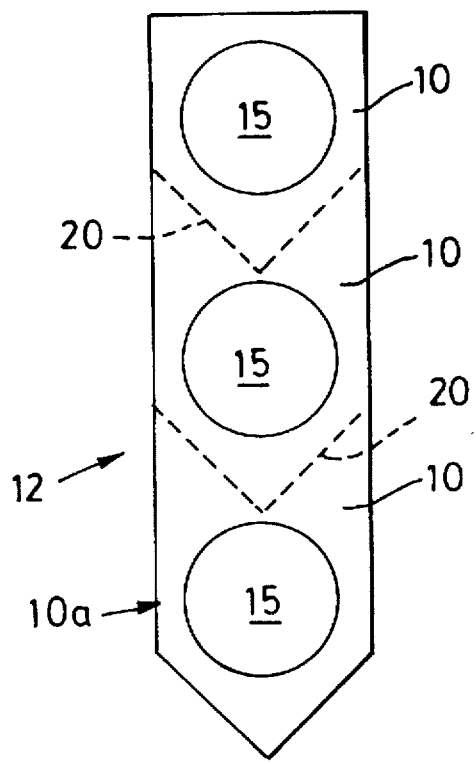
FIG. 1a is a representation of a strip of sample collection tokens in accordance with the present invention.

Referring to FIG. 1a, there is shown a sample collection token made in accordance with the present invention, referred to generally by reference numeral 10. The token 10 is used to collect samples of trace elements from the hands and fingers of individuals, for subsequent analysis. The token 10 may be used to collect samples from any number of different classes of individuals, including airline passengers and medical patients. For example, the token 10 may be used to collect samples from an individual for subsequent analysis to determine whether he or she has recently handled explosives or illicit drugs. Alternatively, the token 10 may be used to collect samples from an individual for subsequent analysis to determine whether certain marker chemicals or metabolites secreted through the skin are present on the fingers of the individual.

The token 10 has a base or substrate including a collection zone 15, on which a sample is collected. The base or substrate may be any suitable material, as described herein. The substrate may be woven or made from a paper-like material or from any appropriate material, to collect a sample of trace particles from the fingers of an individual. Generally, in order to allow subsequent analysis, the substrate must be made from a material which will withstand high temperatures which occur during desorption during subsequent analysis. Further, the substrate must not itself interfere with subsequent sample analysis, or give false readings for the particular analyte being searched for.

A number of different substrates have been evaluated for use in the present invention. Some of the governing criteria were efficiency of particle retention, heat transfer during desorption, low surface interaction between contaminants being monitored and the substrate surface, freedom from absence of interfering contaminants in the substrate and low cost. Criteria used in selecting substrate material are: absence of interference; suppression or false peak identification generated from substrate upon heating; substrate should effectively remove explosives traces or particles containing explosives from fingers/hands; low raw material and manufacturing cost; material should not be susceptible to contamination from ambient air during use and storage; and traces of explosives and/or drugs must be easily desorbed from the substrate.

Also, the suppression effect of various soaps, perfumes and hand creams have been evaluated with each preselected substrate before final selection was made. Three major classes of filter materials were evaluated: glass fibre, Teflon (Registered trade mark), and synthetic fabric materials. Many other synthetic filter materials that are available, like nylon, polyester and their combinations generally cannot withstand the high desorption temperature and therefore are less useful. Commercially available glass fibres that are normally used for filtration and particle collection such A/D, A/C and A/E (Gelman Sciences) and Marminglas (Lydall Inc.) do not have the required physical strength. Although epoxy and Teflon reinforced glass fibre filters have sufficient strength, they suffer from poorly controlled porosity and a high degree of contamination originating from additives for improved strength.

Many types of Teflon filters are available on the market with major variations in their porosity and thickness. Filters examined were Zefluor of various thicknesses (Gelman Sciences), TF (Gelman Sciences), and 50 μm Teflon (Fluorotechnique). All lacked physical strength. All had contaminants in various degrees, and had to be re-baked at 240° C. to clean them. Their efficiency in preconcentration of organic volatiles present in air is very good. Thus a clean filter disc or token could become contaminated in a few minutes when left uncovered in a dirty environment. The most suitable filters were found to be skived Teflon, 0.010" thickness, available from Gulf-Midwest Packaging in Romulus, Mich.

Although wool and silk can withstand higher temperatures than cotton, naturally present contaminants and break down products from fibres under elevated temperature cause considerable contamination. Cotton materials are available with various thicknesses and porosities, but must be pretreated at a high temperature to remove contaminants introduced during manufacturing.

Linen materials withstand higher temperature than any other natural fibre materials but the product is usually thick and expensive, which does not provide any advantages over the cotton material. Thus, Teflon and cotton are the most suitable materials.

The selected cotton material had to be heat pretreated at 240° C. for 40 minutes, to remove any contaminants introduced during manufacturing and naturally present in the cotton. The Teflon filter material had to be also baked when received from the supplier in a manner similar to the cotton treatment. The substrate can be woven and can comprise one of cotton, Teflon, and fibreglass. The token/disc substrate can be chemically treated to enhance its ability to collect and entrap at least one of the desired particles, droplets or other chemicals, and the substrate material can be chemically treated to modify the chemistry thereof during desorption, and pyrolysis cycles.

Figure 2:
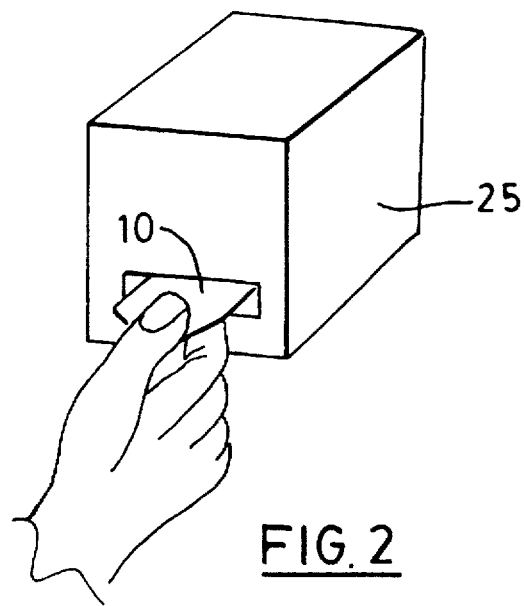
FIG. 2 is a perspective view of a token and a token dispenser in accordance with the present invention.

Referring to FIG. 1a, in one embodiment of the present invention, a number of the tokens 10 are joined together, for example to so as to form a roll (not shown), so as to be easily dispensable from a dispenser 25 (see FIG. 2). In such a case, the tokens 10 are formed in a strip 12, and separated by perforations 20, so that a single token 10 may be removed from the strip when desired. This will be discussed in more detail subsequently.

Prior to being placed in the dispenser 25, it must be ensured that the tokens 10 are not contaminated with any material which could interfere with analysis of a collected sample, or give false readings. One such method of removing contaminants is to heat the tokens 10. The tokens 10 formed from cotton are heated at 240° C. for 40 minutes, which effectively removes any contaminants on the tokens 10, and Teflon needs to be treated similarly.

Once the tokens 10 have been freed of contaminants by the heating process, they are preferably stored in a sealed container (not shown) impervious to contaminants of interest, e.g. explosives and drugs. When it is desired to use them, a roll of the tokens 10 is removed from the sealed container, and placed in the dispenser 25 shown in FIG. 2. The dispenser 25 provides a controlled environment for the tokens 10, and should be sealed as much as possible, so as to protect the tokens from any contaminants which may be present in the ambient air around the dispenser 25. The actual design of the dispenser 25 is not critical, so long as it provides a controlled environment for the tokens 10.

The mechanism in the dispenser 25 is such that only a portion of the next token 10, indicated at 10a in FIG. 1a, projects from the dispenser 25. In other words, no portion of the next token projects, so that it cannot be contaminated by a user grasping the token 10a. The configuration of the outlet of the dispenser 25 should be such as to only permit a user to grasp a token 10 with a thumb and finger, and not permit it to be grasped in any other way. Thus, the dispenser 25 can be fitted with a shield or the like to prevent a user from grasping the two side edges of the token 10. The intention is that a user, forced to grasp the token 10 with a thumb and finger, will be forced to grasp a significant portion of the centre of the token 10, from which a sample is subsequently desorbed.

Further, the dispenser itself should be such as to minimize any possibility of cross contamination from one token to the next. Thus, there should be no elements of the dispenser housing, which form an exterior of the housing and which rub against the tokens. This would then raise the possibility that drug or explosive traces could be left by one person on the housing only to have them removed by a subsequently dispensed token.

Such a token dispenser bears some similarly with dispensers used to dispense numbers and the like for ordering and serving in shops and other locations. For such purposes, it is normally desirable that a number or token ought to be dispensed readily and easily, and hence they are provided with significant perforations. Exactly the opposite is desirable here. Thus, depending upon the material, the tokens 10 are only lightly perforated, so that a user must apply considerable force to remove a token 10. Alternatively, a line of weakness, i.e. a line of reduced thickness, is provided. This forces a user to grasp a token securely and hence transfer an adequate sample of contaminants, body oils, skin particles etc. onto the token.

Thus, in use, a user securely grasps a token between the thumb and finger and separates it from the rest of the token strip. The mechanism inside the dispenser 25 is such that it is reset each time a token is removed, and then automatically causes the next token in the roll to project out ready to be grasped and removed.

When a token 10 is removed from the dispenser 25, a sample is transferred from the fingers of the individual onto the substrate 15. Subsequently, the token 10 is provided for chemical analysis to determine whether the compounds of interest are present on the token 10. Any conventional type of analysis which detects the compounds being screened for may be used, and such analysis does not form part of the present invention.

Here, the tokens are analyzed in an IMS analyzer and may be an analyzer as shown in U.S. Pat. No. 4,405,781 or 5,071,771, the contents of which are hereby incorporated by reference. However, regardless of the type of analysis which is performed, it is critical at this point to prevent contamination by third party handling, such as the operator of the device for analyzing the sample. For example, if the operator handles the tokens directly this may result in cross contamination from one token to another.

Figure 3:
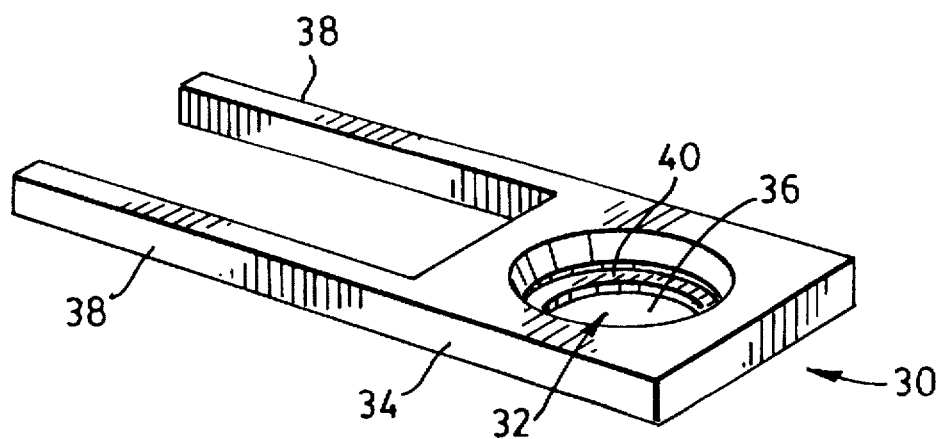
FIG. 3 is a perspective view of a token receiving apparatus, for use in connection with a sample collection token and a token analyzer.

To this end, a token handler 30 may be provided as shown in FIG. 3, which is adapted to be receive a token, and introduce the token into the device used to analyze the collected sample. The token handler 30 has a frame 34, and a receiving area 32 for receiving a token. The receiving area 32 is designed to receive a token 10, and may have a geometrical shape which matches the shape of the token 10. However, this is not essential and the six-sided tokens of FIG. 1a can be used with the circular receiving area 32. The receiving area 32 has an aperture 36, which is preferably smaller in diameter than the width of the token 10, so that a sample collected on either side of the central portion of the token 10 may be analyzed. In order to support the token in the receiving area 36, there is a surrounding lip 40 in the receiving area 32 which supports the token. This prevents circular tokens, discussed below, from failing through the token handler.

A pair of slide rods 38 are located at one end of the token handler 30. The slide rods 38 are provided to support the token handler 30 on the analyzer. In such an embodiment, there is provided a matching pair of bores in the analyzer (not shown).

While the token handler 30 made be made from any appropriate material, the chosen material should be inert and must not interfere with the analysis of the collected sample. Further, the material must be capable of withstanding the high temperatures to which it is exposed during the desorption process.

In this fashion, after the individual has removed a token 10 from the dispenser and thus provided a sample, the individual then places the token into the token handler 30 which is associated with the analyzer. Subsequently, the token handler 30 can correctly position the token 10 for analysis in the analyzer. It will of course be appreciated that the particular design for the token handler is not critical, but a key feature is that it is not required that the token be handled by an individual other than the one from whom the sample was collected.

Figure 4:
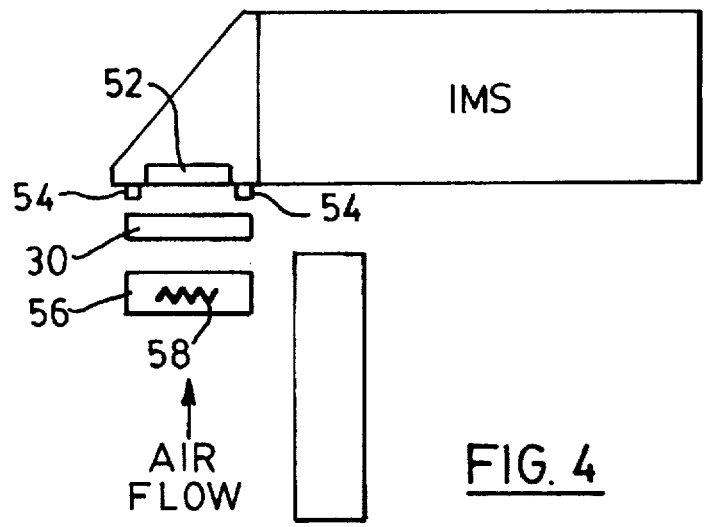
FIG. 4 is a schematic view of an ion mobility spectrometer used to analyze the sample collection token.
Figure 5A:
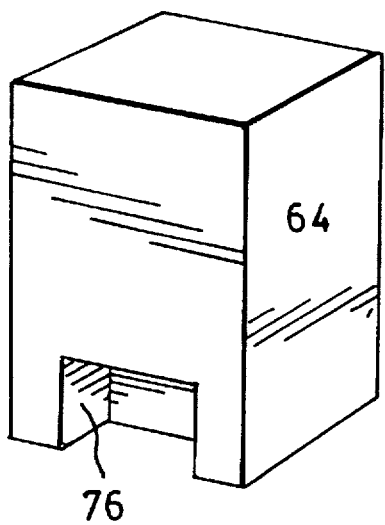
FIGS. 5a and 5b are perspective and sectional views through a dispenser for tokens in accordance with the present invention.
Figure 5B:
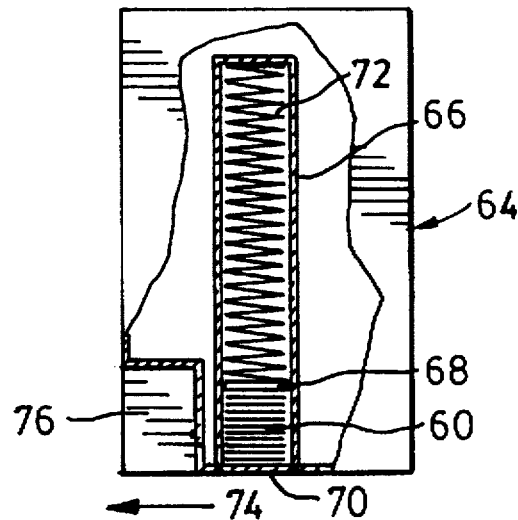

The token handler 30 is used to introduce the token 10 and substrate including the sample to be analyzed into an analyzer 50, which may be schematically represented as seen in FIG. 4. The analyzer 50 shown in FIG. 4 represents an ion mobility spectrometer (IMS). However, it will be appreciated that any type of analyzer may be used which is capable of detecting the compounds being screened for.

In FIG. 4, the IMS analyzer has an inlet 52 into which the sample to be analyzed is introduced. The inlet 52 is appropriately sized to receive a sample of air or inert gas which has been passed through the token and substrate containing the sample to be analyzed. Surrounding the inlet 52 is a seal 54 which forms a seal between the inlet 52 and the token handler 30. The seal 54 is provided to prevent the gas sample from escaping from the IMS analyzer after is passes through the collected sample.

Below the token handler 30, there is located an anvil 56, which is moveable in a vertical direction by a drive means (not shown). The drive means may comprise for example an electromechanical drive. The anvil 56 contains a heater with a heating element 58 for heating the substrate of the token 10.

Once the token handler 30 is in place with a token 10 adjacent the inlet 52, the anvil 56 is raised to come into contact with the token 10 and press the token 10 against the inlet 52. Subsequently, the heater 58 within the anvil 56 is activated, which heats the anvil 56, which subsequently heats the substrate of the token 10. This vaporizes and desorbs the sample from the substrate. Simultaneously, a gaseous flow such as air or another inert gas is passed through the heater 58, to heat the gas, and through the token 10 into the inlet 52 of the analyzer 50. As the sample on the substrate is desorbed and vaporized, the vaporized sample is entrained in the gaseous flow and enters the inlet of the analyzer, where it is subsequently analyzed for the desired compounds.

The dimensions of the working portion of the anvil and the edge portion of the token preferably correspond in size and shape with the size and shape of the inlet 52.

After the desorption process is completed, the token and substrate should be effectively clean from any contaminants, and may be used again, although reuse is only practically applicable to the second embodiment of the token described below. If desired, the entire token may be subjected to another high temperature cleaning phase (as previously described) prior to another use. Alternatively, the token may be discarded after a single use.

Figure 1B:
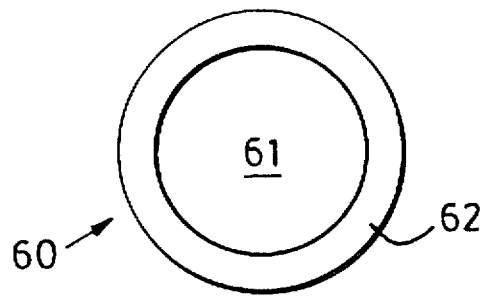
FIG. 1b is a plan view of a second embodiment of a sample collection token in accordance with the present invention.
Figure 1C:
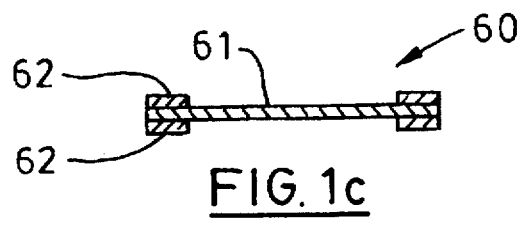
FIG. 1c is a cross-sectional view through the token of FIG. 1b.

FIG. 1b shows an alternative embodiment of the token, designated 60. Shown in FIG. 1c, this second embodiment 60 has a circular substrate portion 61 sandwiched between a pair of annular rings 62. The material of the substrate portion 61 should be chosen so as to provide good adsorption and desorption characteristics. The material for the rings 62 should be selected so as to provide adequate stiffness and support to the token 60 and to promote a good seal around the edge of the token during desorption.

It is anticipated that these tokens 60 would be provided in a stack to be dispensed from a dispenser indicated at 64. Within the dispenser 64, there can be a number of stacks 66 of tokens. Each stack 66 can comprise a tube or the like in which there is a stack of tokens 60. A pressure member 68 applies a uniform pressure or load to the top of the stack of the token 60, which is supported at the bottom as indicated by a support 70. The pressure mounter 68 can be a simple weighted disk or a spring indicated at 72.

The support member 70 is such as to support the edge of the lowermost token 60 through approximately a semicircle while leaving the lowermost token 60 free to slide forward in a direction indicated by the arrow 74. It can also be noted that the dispenser 64 is provided with a recess 76, which may be incorporated in the dispenser 25. This recess 76 encourages correct grasping of the token 60.

In use, a user must first engage the bottom of the lowermost token 60 with his or her forefinger and pull or slide the token 60 forward, so that its edge protrudes into the opening 76. The top of the token 60 can then be grasped between the thumb and the forefinger and the token slid out fully in the direction of arrow 74. It must be appreciated that the recess 76 ensures that the thumb and forefinger are used to grasp the token 60, and this procedure ensures that a user must necessarily firmly grasp the token 60 and leave a significant deposit on both sides of it. To this end, the resistance provided by the mechanism should be such as to enable the token 60 to be readily dispensed, but at the same time to ensure that a user must apply sufficient pressure to leave a good sample.

It will be appreciated that the circular token 60 can be dimensioned to fit exactly within the receiving area 32 of the token handler 30. The lip 40 can be dimensioned to correspond to the annular ring 62. In use, when the token handler 30 is inserted into the analyzer, the annular ring 62 would be sandwiched between the lip 40 and the sealing ring 54, thereby ensuring an excellent seal, so as to minimize sample loss or entrained ambient air.

While the use of the token described herein has been with an IMS analyzer, it will be appreciated that any number of analytical means may be used to screen for desired compounds.

While preferred embodiments have been described, it will be appreciated that numerous variations and modifications are possible within the scope of the present invention. In particular the token, whether in the form of a disc or card, can be dispensed in various ways. It is also to be appreciated that the substrate can be composed of electrically conducting fine mesh, of a size appropriate to trap the particle range to the collected. Then the conductive mesh substrate can be used directly in a desorbing stage in which the particles are flash desorbed by the rapid heating of the metal mesh by the passage of electric current through it. The substrate can also be such as to attract and hold particles electrostatically.

The collection token is preferably presented to the analyzer by inserting the token into a slot of matching geometrical shape and size in a token handler which is then transposed to the desorption stage, so no intermediate sample transfer step is required. A key benefit of controlling the geometry of the substrate surface which contacts the surfaces under inspection is that the substrate profile can be made to match the analyzer inlet geometry perfectly. That is, the token can be configured so that the analyte is centrally collected on the token and correspondingly aligned and presented to the analyzer. The IMS analyzer has sufficient sensitivity for the detection of the desired analytes, and their identification is pre-programmed into the IMS analyzer. Analyzers such as the IMS have been well described in the literature and in patents. While the invention is described in terms of analysis using IMS, it will be apparent to those experienced in the art that the substrates can be made into forms and shapes suitable for introduction to other types of analyzers, such as gas chromatographs or chemiluminescent detectors, mass spectrometers and the like.

We claim:

1. A method of collecting a sample from the hand of an individual for analysis, the method comprising:
   (a) dispensing a token, which includes a substrate defining an area for contact with the fingers of the individual;
   (b) having the individual manually grasp and remove said token, thereby transferring a sample from the fingers of the individual to said substrate;
   (c) having the individual release the token; and
   (d) delivering the token to an analyzer and analyzing the sample on the token, to determine whether said sample includes a predetermined analyte.

2. A method as claimed in claim 1, wherein the token is dispensed by a mechanism which requires a substantial force to be applied to the token to remove the token, whereby the individual must firmly grasp the token, thereby causing adequate transfer of the sample to the token.

3. A method as claimed in claim 2, wherein the token is dispensed from a dispenser containing a plurality of tokens, and after each token is dispensed, a further token is presented for removal by another individual.

4. A method as claimed in claim 3, wherein the plurality of tokens are provided as a continuous strip, and the step (a) of dispensing a token comprises dispensing a token from an end of the strip.

5. A method as claimed in claim 3, wherein the plurality of tokens are provided in at least one stack, and wherein step (a) comprises dispensing a token from the bottom of the stack of tokens.

6. A method as claimed in claim 3, when carried out using tokens formed from a material which is selected to show no interference or suppression to the predetermined analyte of interest, is efficient at adsorbing a sample, and is not contaminated by ambient air compounds, readily desorbs substances of interest and can withstand high desorbing temperatures.

7. A method as claimed in claim 6, which includes at least one of the additional steps of:
   (1) cleaning and pretreating the tokens by one of baking, washing and solvent treatment to remove possible interferents or other impurities; and
   (2) pretreating the material of the tokens by impregnation with at least one of a solvent and surface active chemicals to enhance the transfer of the predetermined analyte from the individual's hand to the token, or to trap and selectively to adsorb the predetermined analyte.

8. A method as claimed in claim 6, when carried out using tokens formed from material which is at least semiporous, and wherein step (d) includes passing a flow of sample gas through the token to entrain the predetermined analyte and subsequently passing the gas flow into the inlet of the analyzer.

9. A method as claimed in claim 8, when carried out using tokens which are made of a material capable of withstanding the application of heat sufficient to remove any undesired chemicals from the token prior to transfer of the sample from the fingers of the individual to the substrate.

10. A method as claimed in claim 9, when carried out using tokens made from material selected from the group consisting of polytetrafluoroethylene, cotton, glass fibres, linen, paper, wool and silk.

11. A method as claimed in claim 4, wherein the strip of tokens comprises a plurality of tokens joined together along lines of perforation, said perforations being dimensioned to provide resistance which must be overcome with a force sufficient to remove one token from the dispenser, thereby causing the individual to firmly grasp said one token.

12. A method as claimed in claim 2, wherein, subsequent to step (d), the token is subjected to thermal desorption to cause release of the predetermined analytes in a short desorption time, to provide a pulse of the predetermined analyte into the analyzer.

13. A method as claimed in claim 12, wherein, in step (c), the individual releases the token and places the token on a token handler, and step (d) comprises delivering the token handler with the token to the inlet of the analyzer.

14. A method as claimed in claim 2, wherein the results of step (d) and the detection of the predetermined analyte is used to provide at least one of (i) control of the opening and closing of access devices; and (ii) warning messages, or other output signals.

15. A method as claimed in claim 14, wherein the results of step (d) are used to control opening and closing of one or more of: a turnstile, a man trap, a security screening booth, and a door.

16. A method as claimed in claim 15, wherein step (d) is carried out in an analyzer selected from the group consisting of ion mobility spectrometers, gas chromatographs, liquid chromatography analyzers and mass spectrometry analyzers.

17. A method as claimed in claim 2, wherein a tracer material, which is not readily detectable, is deposited on objects to be monitored, which tracer material is readily transported by the individual's hands to the token, whereby the method can detect if the individual has been in contact with the objects being monitored.

18. A method as claimed in claim 2, when carried out using a token formed from one of a metal cloth and material having a conductive coating thereon, to facilitate electrical heating to achieve rapid thermal desorption.

19. A method as claimed in claim 2, wherein the token is first treated with a substance to preferentially enhance analysis of the predetermined analyte which may comprise different chemical families present together.

20. A method as claimed in claim 2, wherein each token is identified by an identification marking, optionally comprising one of a number and a bar code so as to associate the individual to the measurement from an individual token, and optionally to at least one of a boarding pass, an entry procedure and passage in a controlled manner through a screening process.

21. A method as claimed in claim 2, wherein in step (d), the token is subject to one of a multiplicity of desorption temperatures and a temperature ramp to selectively release a plurality of predetermined analytes at different temperatures to facilitate the analysis process.

22. A method as claimed in claim 2, wherein each token comprises a plurality of portions joined together along lines of weakness, optionally comprising lines of perforation, to permit the portions to be separated from one another, thereby enabling each portion to be handled and analyzed separately, wherein in step (d) just one portion of the token is delivered to the analyzer.

* * * * *